United States Patent [19]
Fitch

[11] Patent Number: 5,730,140
[45] Date of Patent: Mar. 24, 1998

[54] SONIFICATION SYSTEM USING SYNTHESIZED REALISTIC BODY SOUNDS MODIFIED BY OTHER MEDICALLY-IMPORTANT VARIABLES FOR PHYSIOLOGICAL MONITORING

[76] Inventor: William Tecumseh S. Fitch, 421 E. 78th St., #1-D, New York, N.Y. 10021

[21] Appl. No.: 432,046

[22] Filed: Apr. 28, 1995

[51] Int. Cl.$^6$ .............................................. A61B 5/0205
[52] U.S. Cl. ................................................ 128/701; 128/710
[58] Field of Search ......................... 364/413.03, 413.04, 364/413.02; 128/671, 670, 701, 710, 920, 923; 600/28

[56] References Cited

U.S. PATENT DOCUMENTS

| | | | |
|---|---|---|---|
| 3,199,508 | 8/1965 | Roth | 128/2.06 |
| 3,215,136 | 11/1965 | Holter et al. | 128/2.06 |
| 3,229,687 | 1/1966 | Holter et al. | 128/2.06 |
| 3,338,234 | 8/1967 | Kleinerman | 128/2.06 |
| 3,513,832 | 5/1970 | Klemm et al. | 128/671 |
| 3,534,728 | 10/1970 | Barrows | 128/2.06 |
| 3,565,058 | 2/1971 | Mansfield | 128/2.06 |
| 3,572,316 | 3/1971 | Vogelman et al. | 128/2.05 |
| 3,613,670 | 10/1971 | Edenhofer | 128/2.06 F |
| 3,615,162 | 10/1971 | Barber | 181/0.5 |
| 3,650,264 | 3/1972 | Janssen | 128/2.06 |
| 3,658,060 | 4/1972 | Eklof | 128/2.05 |
| 3,732,868 | 5/1973 | Willems et al. | 128/2.06 |
| 3,742,937 | 7/1973 | Manuel et al. | |
| 3,760,100 | 9/1973 | Ragsdale et al. | 179/1 R |
| 3,769,965 | 11/1973 | Raddi et al. | 128/2.05 R |
| 3,830,227 | 8/1974 | Green | 128/701 |
| 3,841,315 | 10/1974 | Kopp | 128/701 |
| 3,888,233 | 6/1975 | Ware | 600/28 |
| 4,015,237 | 3/1977 | Takatani et al. | 340/52 F |
| 4,224,613 | 9/1980 | Kaiser et al. | 340/679 |

(List continued on next page.)

FOREIGN PATENT DOCUMENTS

0005282  7/1988  WIPO ........................ 128/671

OTHER PUBLICATIONS

Albers, Michael C., "Auditory Cues for Complex, Supervisory Control Systems: Aiding Fault Detection and Isolation in Satellite–Ground Control", Center for the Human–Machine Systems Research/Georgia Institute of Technology. 1994 CHI Workshop.

Fitch et al., "Sonifying the Body Electric: Superiority of an Auditory over a Visual Display in a Complex, Multivariate System", Auditory Display, Ed. Gregory Kramer, SFI Studies in the Sciences of Complexity, Proc. vol. XVIII, Addison–Wesley, 1994, pp. 307–325.

(List continued on next page.)

*Primary Examiner*—Wm. E. Kamm
*Assistant Examiner*—Kennedy J. Schaetzle
*Attorney, Agent, or Firm*—Pennie & Edmonds LLP

[57] ABSTRACT

A method and apparatus are described for converting physiological information into sound, suitable for such applications as anesthesiological, intensive-care or exercise monitoring. Complex, realistic bodily sounds (e.g., heartbeat sound and/or breathing sound) are synthesized algorithmically, and directly reveal certain physiological variables such as heart rate or breathing rate. Changes in other physiological variables (e.g., blood pressure or carbon dioxide level) are indicated by changes in acoustic parameters of the realistic sound (e.g., pitch or timbre). A large number of these "piggyback" variables can be made audible by controlling a plurality of acoustic parameters simultaneously, taking advantage of the ability of the auditory system to process large quantities of information in parallel. The combination of realistic sounds with "piggyback" variables provides a novel means of monitoring physiological data with advantages over both the visual monitoring systems currently in widespread use and other proposed and existing sonic monitoring systems. Other improvements to existing sonification methods are taught, including "self-labeling" alarms and auxiliary sound mix-through.

12 Claims, 10 Drawing Sheets

System Overview

U.S. PATENT DOCUMENTS

| | | | |
|---|---|---|---|
| 4,576,178 | 3/1986 | Johnson | 128/701 |
| 4,653,498 | 3/1987 | New, Jr. et al. | 128/663 |
| 4,785,280 | 11/1988 | Fubini et al. | 340/52 F |
| 4,868,869 | 9/1989 | Kramer | 381/61 |
| 4,896,675 | 1/1990 | Ohsuga et al. | 128/671 |
| 4,949,274 | 8/1990 | Hollander et al. | 364/483 |
| 4,996,409 | 2/1991 | Paton et al. | 219/130.01 |
| 5,309,908 | 5/1994 | Friedman et al. | 128/633 |
| 5,343,871 | 9/1994 | Bittman et al. | 128/670 |
| 5,360,005 | 11/1994 | Wilk | 128/653 |
| 5,371,854 | 12/1994 | Kramer | 395/2.79 |

OTHER PUBLICATIONS

Gaver, William W., "Using and Creating Auditory Icons", Auditory Display, Ed. Gregory Kramer, SFI Studies in the Sciences of Complexity, Proc. vol. XVIII, Addison–Wesley, 1994, pp. 417–446.

Schulte et al., "Can People Hear the Pitch Change on a Variable–Pitch Pulse Oximeter?". From the Dept. of Anesthesiology, The Ohio State University, Journal of Clinical Monitoring, 1992; 8, pp. 198–200.

Fitch et al., "Sonifying the Body Electric: Superiority of an Auditory over a Visual Display in a Complex, Multivariates System". Presentation at the first International Conference on Auditory Display, Santa Fe, New Mexico, Oct. 1992.

Rabenhorst, et al., "Complementary Visualization and Sonification of Multi–Dimensional Data". IBM Research Division, Research Report, RC 15467, Jan. 1990, Computer Science 7 pages.

Posner et al., Chapter 15, "Unintended Thoughts: Intentional Chapters on Unintended Thoughts", Guilford Press, 1989, pp. 450–469.

Johnson, David, "A New Monitoring System That Relies on Sound". Biomedical Technology Today, May/Jun. 1988, pp. 83–84.

Sorkin et al., "Why Are People Turning Off Our Alarms?" Dept. of Psychological Sciences, Purdue University; Journal of Acoustical Society of America, Sep. 1988, pp. 1107–1108.

Sorkin et al., "Likelihood Alarm Displays", Human Factors, 1988, 30(4), pp. 445–449.

Patterson, Roy D., "Guidelines for Auditory Warning Systems on Civil Aircraft" Civil Aviation Authority London, CAA Paper 82017, Nov. 1982.

Yeung, Edward S., "Pattern Recognition by Audio Representation of Multivariate Analytical Data". Analytical Chemistry, vol. 52, No. 7, Jun. 1980, pp. 1120–1123.

Pollack et al., "Information of Elementary Multidimensional Auditory Displays". The Journal of the Acoustical Society of America, vol. 26, No. 2., Mar. 1954, pp. 155–158.

Forbes, T.W., "Auditory Signals for Instrument Flying". Journal of Aeronatical Sciences, May 1945, pp. 255–258.

Fig. 1: System Overview

Fig. 2: Input Processer 10

Fig. 3: Alarm Processing Unit 20

Fig. 4: Mapping Unit 30

Fig. 5B: Unit Generator 51

Fig. 5A: Synthesizer 50 (General)

Fig. 5C: Synthesizer 50 (Heart Sound)

Fig. 5D: Synthesizer 50 (Breathing Sound)

Fig. 6: Audio Output 60

Fig. 7: Alternative User Interfaces

Type 1: Command Line Interface (Computer)

```
> set threshold heart_rate max 150
```

Type 2: Graphical User Interface (Computer)

Type 3: Physical Interface (Dedicated Hardware Implementation)

SONIFICATION SYSTEM USING SYNTHESIZED REALISTIC BODY SOUNDS MODIFIED BY OTHER MEDICALLY-IMPORTANT VARIABLES FOR PHYSIOLOGICAL MONITORING

BACKGROUND OF THE INVENTION

1. Field of the Invention

This invention relates generally to the field of measuring and testing and data comprehension and, particularly, to a method and apparatus for using sound to monitor physiological data.

2. History of the Field and Prior Art

A. General Issues in Sonification

"Sonification" is the use of non-speech sound to communicate data. The field of sonification is not new, and important contributions to the field were made as early as the 1950's. Sonification provides an alternative to visual means of communicating data (such as graphs, computer monitors and other visual displays), providing a data interface for users whose eyes are occupied with other tasks, or for blind users. Processing differences between the visual and auditory systems make appropriately-designed sonic displays better-suited for certain tasks than comparable visual displays which currently dominate (e.g., the human auditory system is better-suited to monitoring many variables simultaneously).

Nonetheless, nearly half a century after Pollack and Ficks' groundbreaking demonstration of the viability of sonification in 1954, and following a host of experimental demonstrations and a number of issued patents, the field remains almost exclusively in the laboratory, with few or no commercially successful or widely-used sonification systems available which live up to the promise of the field. Why?

A sonification system must fulfill at least two requirements in order to achieve success: it must be accessible (open to productive use without overly demanding training), and it must be powerful (its ability to pass a significant quantity of information to the user rapidly and accurately must be comparable or superior to corresponding visual displays). Sonification systems currently exist that fulfill one or the other of these requirements, but none fulfill both. For example, the use of realistic or "iconic" sound in computer interfaces pioneered by William Gaver (e.g., Gaver, 1989) results in a sonic interface which is highly accessible due to the instant recognition of the sounds used. However, the use of pre-recorded or "sampled" sound severely limits the flexibility and power of such interfaces (Gaver, "Using and Creating Auditory Icons", in G. Kramer (Ed.), Auditory Display (Addison-Wesley 1994). Such a system tends to be interpreted very literally, and serves best as an add-on to visual displays (e.g., for "virtual reality" systems). In contrast, the use of abstract, non-representational sounds (synthesized musical sounds such as tones, beeps, pulse trains and buzzes: Pollack & Ficks, "Information of Elementary Multidimensional Auditory Displays", J. of Acoustical Society of America, 26(2), pp. 155–158 (1954), Johnson, U.S. Pat. No. 4,576,178) provides excellent flexibility and power: it is a simple matter to vary many acoustic parameters of such synthesized sounds and thus pack a large quantity of arbitrary information into a single sonic event. However, this very flexibility typically leads to systems which are annoying, confusing and difficult to master. All currently-available sonification systems fall into one or the other of these categories, and thus suffer from one or the other of the limitations discussed above.

A second important issue which permeates the literature on sonification concerns the degree of preprocessing performed by a sonification system: the extent to which the system analyzes, classifies or otherwise processes the input data before converting it to sound. In the most extreme case, the sonification method classifies the input data and uses a speech synthesizer to verbally report its classification. Such a system would not even be considered sonification by most researchers due to its complete reliance upon speech as a transmission medium. More typically, some sonification researchers have proposed quantizing the input signal, such that continuous change in the input variable is output as discrete change in the sonic variable. For example, Johnson's U.S. Pat. No. 4,576,178 teaches a sonification system which processes a continuously-varying input signal through a step function creating an output that varies in n discrete steps. Johnson argued that this approach makes changes easier to note, further suggesting that "small changes in a continuously varying output signal . . . might not be noticed at all".

Substantial evidence from the fields of auditory psychophysics and cognitive science suggests that these approaches are wrong-headed because they underestimate and under-use the processing power of the auditory system. Mounting data indicates that human perceptual systems such as the auditory or visual system are best viewed as powerful information processing systems with many interlocking components (Fodor, The Modularity of Mind (MIT Press 1983), Bregman, Auditory Scene Analysis: The Perceptual Organization of Sound (MIT Press 1990)). Many, if not most, of these components are "cognitively impenetrable": they are inaccessible to conscious control and often unavailable to conscious experience. Nonetheless, they are continually processing information and the results of their computations influence and direct the higher-level cognitive components which underlie our conscious experience. The classic phenomenon leading to this view is called "blind sight", in which damage to high-level visual areas in the brain results in patients who experience complete blindness but are nonetheless able to orient to visual objects, and sometimes even catch objects thrown to them. A more commonplace example is our habituation to low level fan noise and electrical hum which permeates most working spaces. Such ambient noise is not typically noted consciously or attended to, but if it changes or disappears, we instantly become aware of it, demonstrating that an unconscious portion of our auditory system was attending. Sonification systems which over-classify or quantize their input data will fail to make full use of this low-level computational machinery, and thus fail to make use of the full processing power of the auditory system.

Further problems plague sonification systems which over-process their input signals. For example, it is obvious that any system which uses sampled speech or speech synthesis to convey information is limited to users who speak the language used. More subtly, but equally important, a sonification system which uses musical sounds, rhythms or harmonic patterns will engage a whole cognitive system of musical expectations and beliefs in the mind of the listener. Although engagement of cognitive modules specific to music may be advisable in some cases ("earcons" as described in Blattner et al., "Sonic Enhancement of Two-dimensional Graphics Displays", in G. Kramer (Ed.) Auditory Display (Addison-Wesley 1994)), it will bias the system towards users with highly-developed musical skills (Brewster et al., "A Detailed Investigation into the Effectiveness of Earcons", in G. Kramer (Ed.) Auditory Display (Addison-Wesley 1994)). Furthermore, musical structures may carry with them unwanted associations that have nothing to do with, or even conflict with, the meaning of the input data. For example, the quantization of pitch into a musical scale as taught by Johnson (U.S. Pat. No. 4,576,178) results in various harmonic intervals to be output by the system. A particular increase in the input data (for example, an increase in blood pressure) will lead to a jump in pitch of three musical half-steps (a "minor third"), while a greater increase in blood pressure would result in a pitch increase of four half-steps (a "major third"). In Western music, a minor third has a somber tone universally associated with sadness, while a major third has a cheery, happy sound. Virtually any listener will experience this association, not just musically trained individuals. The larger increase in blood pressure in the second example is potentially more dangerous than the first, but the incidental musical associations which result from quantization lead to the unwanted and misleading conclusion that it is happier or safer. Finally, even if a sonification system were specifically designed to make use of such musical associations, its usefulness would depend on the musical and cultural background of the user. Thus, a user who listened mainly to jazz might find certain intervals pleasing (e.g., blue notes, flat 5 intervals, etc.) which would seem unpleasantly dissonant to a user who listened only to Bach. Such differences would be even more extreme with listeners familiar with completely different musical traditions, e.g., Chinese, African or Indian musical styles. Thus, classifying, quantizing or otherwise overly-preprocessing the input in a sonification system can not only deprive the user's auditory system of useful information, but also lead to a host of complications and undesirable side-effects due to musical associations.

B. Alarms and Annoyance Issues

It may seem strange given the points raised in the previous section that the most common form of auditory display, the audible alarm, is an extremely classificatory device. Most alarm devices, from smoke detectors to nuclear power plant warning systems, are one-bit classifiers: they are either on or off, and give no graded information about the severity or nature of the danger. While such simple systems may be adequate for certain low-risk situations, there is evidence that this approach is dangerously inadequate. For instance, operators in the 1987 Amtrak-Conrail train catastrophe had disabled the warning whistle in the locomotive, presumably because it produces a very loud, aversive, shrill sound and is prone to false alarms. An investigation conducted shortly thereafter found six other taped-over warning whistles, even though 24-hour notice of the inspection had been given. Sorkin, "Why Are People Turning Off Our Alarms?" J. Acoustical Society of America, 84(3), pp. 1107–1108 (1988) gives many more example of auditory alarms being ignored or disabled, contributing to catastrophes as diverse as the successful Iraqi attack on the USS Stark, the Northwest Airlines Flight 255 disaster, and accidents in the nuclear power industry.

Given the frequency and severity of such disasters, improvements in alarm design could clearly be of significant benefit to society. Why do operators disable or ignore auditory alarms? One reason is that the sounds produced are typically annoying or even aversive to the point of interfering with normal cognition or communication. Thus, after completing their intended function of alerting the operator to a problem, they perform the unintended function of hindering its solution. A second reason is a high false-alarm rate, which leads to a lack of faith in the warning system and a casual attitude to alarm occurrence on the part of human users (a "cry-wolf" syndrome). Finally, alarms which provide redundant or insufficient information will come to be viewed as a useless annoyance by users; when warnings are expected on commercial aircraft, crew members are sometimes assigned to sit poised to hit the cancel button the moment the alarm goes off (Patterson, "Guidelines for Auditory Warning Systems on Civil Aircraft" (CAA Paper 82017) (Civil Aviation Authority 1982).

These problems all result from a lack of attention to the human half of the human/machine interface. For the alarm designer, a system which generates occasional false-alarms (but never misses a real emergency) is a prudent way of avoiding lawsuits. However, when the entire system (including the human operator(s)) is considered, such a system will yield poor performance, since it will "train" the human user to ignore it (Sorkin & Woods "Systems with Human Monitoring: A Signal Detection Analysis," Human-Computer Interaction, 1, 49–75 (1985)). Similarly, alarms which are annoying and uninformative will be viewed as disturbances by operators, who will then seek to turn them off. Thus when the human/machine system is viewed as a whole, an adequate alarm should be accurate, informative and alerting without being annoying.

A further annoyance issue of serious concern in sonification stems from the fact that we are anatomically unable to "close our ears" as we can our eyes. A sonification system may thus reach ears for which it is not intended, and interfere with others' work. Although headphones can be worn by the system user, these can be obnoxious over long periods, and may interfere with other tasks requiring unhindered hearing. Additionally, simultaneous sounds can become confused and garbled (so a sonification system's output might interfere with speech or recreational sounds like music or radio shows). A sonification system which interferes with the normal sonic environment of the workplace will be viewed as annoying, and may be rejected or disabled for that reason.

C. Physiological Monitoring

The issues discussed in the previous section apply to sonification in general; we now turn to issues specific to physiological monitoring, that is, monitoring the ongoing vital functions in living organisms. Physiological monitoring is an ideal application for sonification, particularly of the type taught in this patent for several reasons. First, there are many types of body sounds which may be realistically synthesized (e.g., heart beat, breathing, coughing, chewing, digestive and excretory noises, etc.), and many of these sounds convey extremely important information. Second, in many of the situations requiring physiological monitoring (surgical or anesthesiological applications, exercise monitoring), the user needs to visually focus on tasks other than monitoring, making auditory monitoring via sonification an ideal alternative to visual monitors. Finally, the serious life-or-death nature of patient monitoring in the operating room provides a strong incentive for adopting new technology: the purchase of a sonification system would be justified by a single life saved. Thus, the current discussion will focus on the operating room application.

Perhaps because of these factors, there are a number of patents teaching the use of sound for patient monitoring (though surprisingly little academic research). Virtually all of this prior art suffers from a drastic limitation in the number of physiological variables which can be conveyed by the system (one or two) due to the nature of the synthesis techniques adopted. Because a large number of physiological variables are critical in actual patient monitoring during surgery or intensive care (see below), a truly powerful medical sonification device would be able to convey most or all of these variables via sound, thus freeing the user from the necessity of looking up at visual monitors to determine the patient's vital signs. None of the systems described in the prior art are able to provide all of the information required in an understandable way.

Although it might theoretically be possible to simply combine a number of these systems to increase the number of variables sonified, this is an inadequate solution and is not done in practice because the sounds and techniques used in the prior art overlap significantly and would be confusing and mutually disruptive. While the system Johnson's U.S. Pat. No. 4,576,178 is capable of sonifying enough variables to give attending medical personnel information on all the important vital signs, his system suffers from other problems: it uses quantization (as discussed earlier), and teaches the use of acoustic pulse-train synthesis, which produces an unpleasant sound and has no imitative, intuitive or easily-memorable relationship to the data being expressed. None of the prior art teaches the virtues of using complex, continuous, realistic or imitative sounds for physiological sonification, nor recognize the flexibility, power, ease of learning and use, and memorability of this technique. These virtues become particularly important in a field like patient monitoring, where a mistake made due to a confusing sonic display could prove fatal.

As a result of limitations of this type, only one physiological sonification device has come into widespread use: the pulse oximeter (e.g., U.S. Pat. No. 4,653,498, issued 1987). An oximeter is a device for measuring the oxygen saturation of the blood, and many such devices generate a tonal acoustic pulse at every cardiac pulse recorded at the fingertip, and vary the pitch of this sound to indicate oxygen saturation. Due to the extreme importance of maintaining blood oxygen at an adequate level (for instance, to avoid brain damage), these devices have come into widespread use, and are seen as lifesavers by many physicians (and their use is even required by some malpractice insurance companies). While this success clearly indicates the promise of sonification in the operating room, pulse oximeters are unable to fulfill this promise: the simple nature of the sound synthesis techniques used renders them incapable of sonifying more data, and none of the pulse oximeter patents even discusses the possibility of sonifying additional variables, nor of using more complex sounds to do so. This is despite an obvious pressing need to monitor many more variables than pulse rate and oxygen saturation.

A large number of physiological variables are critical in assessing patient status during surgery or intensive-care monitoring. At a minimum, heart rate, blood oxygen, blood pressure, respiratory rate and exhaled carbon dioxide are necessary to evaluate cardiac and respiratory function and are continually monitored by medical personnel during surgery and recovery. A wide variety of additional variables may also be monitored, depending on the nature of anesthesia, type of operation, and illness of the patient (see for example, Chung & Lam, Essentials of Anesthesiology (Saunders 1990), including electrocardiogram, ventilatory volume, anesthetic machine airway pressure and gas concentrations, body temperature, urinary output, blood sugar and gases, and many others. Thus, an adequate physiological sonification system should be capable of coding at least five, and more typically 6 to 10, variables in order to convey all the important physiological data through sound. Furthermore, such a system should code this data in a way which is easy to learn, difficult to confuse, and pleasant to listen to over long periods of time.

BRIEF DESCRIPTION OF THE INVENTION

Accordingly, several objects and advantages of the present invention are: (a) to provide a sonification system which is both accessible (easy to learn and use) and powerful enough to compete with visual displays; (b) to provide a sonification system which uses synthesized realistic sound to provide accessibility and ease of use, and modifies specific acoustic attributes of this realistic sound in accordance with different input variables to provide flexibility and power; (c) to provide a sonification system which allows full beneficial use of the human auditory perceptual system and is not limited by the language, musical background or musical skill of the user; (d) to provide a sonification system which avoids having quantization, classification or other fixed algorithmic decision processes from limiting the information conveyed by the sonification process, though remaining amenable to the addition of alarms or other classificatory indicators of status; (e) to provide a sonification system whose sounds are not annoying and aversive, and in which the information provided is rarely redundant or insufficient; (f) to provide a sonification system which does not interfere to a disruptive degree with the sonic environment in which it is used; (g) to provide a physiological sonification system which meets the above goals, and further allows its users to monitor all of the critical physiological variables by sound alone, typically including heart rate, breathing rate, blood oxygen saturation, blood pressure and exhaled carbon dioxide level. Further objects and advantages will become apparent from a consideration of the ensuing description and drawings.

The current invention meets these goals by hybridizing realistic and abstract sonification techniques, synthesizing realistic sounds and then modifying their acoustic parameters both in a literal way (using input data directly related to the acoustic parameter(s) changed) and in an abstract way (using input data only arbitrarily related to the acoustic parameter(s) changed). Although such an approach could combine the worst features of the two approaches, successful application of the technique (demanding expertise in cognitive science, sound synthesis and the type of data being sonified) results in a wide variety of sonification systems which combine the accessibility of realistic sounds with the flexibility of abstract sounds.

In a preferred embodiment of the invention, the sonification system synthesizes two realistic "base streams": a heart sound and a breathing sound. These sounds are not only readily identifiable, reasonably pleasant and acoustically well-suited to the task, but all of their acoustic parameters can be independently controlled (rate, rhythm, duration, pitch, loudness, spatial location, and timbre). In particular, some physiological variables which have acoustic properties of their own such as those related to timing can be used to alter the heart sound or breathing sound in a way that is directly or literally reflective of the physiological variable. For example, the repetition rate and the duration of the heart sound can be made to be the same as the corresponding measured physiological variables of the patient as determined from an EKG or a pulse signal; and the repetition rate of the breathing sound can be made to be the same as the corresponding measured physiological variable of the patient as determined from a respirometer, a volumeter or similar device. Other physiological variables, called "piggyback" variables because they "ride" the base streams, are used to control other acoustic parameters of the base stream sounds which may be only arbitrarily related to the physiological variable. For instance, the pitch of the heart sound can be controlled by oxygen saturation (as made popular in the pulse oximeter), and heart sound timbre ("tone quality") can be controlled by blood pressure (appropriate because blood pressure is another measure of cardiac functioning). Exhaled carbon dioxide, as measured by a capnometer, can control breathing sound "pitch" (more specifically, the center frequency of the band-pass filter in the breathing sound synthesis circuit), as befits its role as a measure of respiratory function. Of course, a physiological variable which does have acoustic properties of its own could be represented as a piggyback variable if desired. In this manner, the system easily codes the five most critical physiological variables in a manner which is clearly audible and simple to learn and remember (as shown experimentally in Fitch & Kramer, "Sonifying the Body Electric: Superiority of an Auditory Over a Visual Display in a Complex Multi-variate System", G. Kramer (Ed.) Auditory Display (Addison-Wesley 1994), which is incorporated herein by reference.

In general, the output parameters of the sonification system are controlled as functions of one or more corresponding physiological variables. Typically, the output is a specific monotonic function determined on the basis of the desired output characteristics. In a preferred embodiment, the output parameter is a linear function of one or more physiological input variables, and in the case of repetitive patterns, the functional relationship can be identity. It would also be possible to use a more complex function to relate input parameters to output parameters. Such a function can be used to compensate for some human psychometric function (e.g., the Fletcher-Munson equal loudness curve), thus relating equal changes in the input variable(s) to equal perceptual changes in the output parameter(s), or a function which combines several input variables to affect a single output variable.

The breathing and heart sounds are an excellent combination acoustically, because they have little acoustic overlap: the breathing sound, roughly, is continuous filtered noise, while the heart sound is a periodic, tonal event. Due to their realistic nature, both sounds have many additional acoustic parameters which can be varied other than those already mentioned. For instance, the heartbeat sound is a dual "thump-thump", and each of these sounds can code different information. Similarly, the inspiration and expiration sections of the breathing cycle can code separate variables. Furthermore, "timbre" is a complex and multidimensional attribute (Grey, "An Exploration of Musical Timbre" Ph.D. Thesis (Stanford Univ. 1975), and the advanced user could use different axes of timbral change to code different variables. Likewise, the filter(s) in the breathing sound circuit can be modified in terms of both center frequency ("pitch") and bandwidth ("breadth").

Although loudness and spatial location can easily be used in this system (and are widely used in other sonification systems), these variables must be used with care because they are highly sensitive to the listener's location and orientation, and thus can be disrupted by the user's movements. If loudness is used, relative loudness is probably preferable, that is, the relative loudness of the two heart beats would be a more reliable parameter than absolute loudness. Although the five critical variables would typically be sonified in a standard configuration, as described above, additional physiological variables can be mapped to these extra acoustic "slots" in a manner dependent on the type of operation, illness and anesthesia. For instance, if a patient is connected to a constant-flow ventilator (which "breathes" for the patient), airway pressure is a key variable, while if a patient breathes for him or her self, depth of respiration is crucial. Either of these can be mapped to filter bandwidth, at the choice of the user.

Although we discuss heart and breathing sounds in this preferred embodiment, one skilled in the art could easily adapt other realistic sounds as well. For example, a common and serious problem in anesthesiology is vomiting by the unconscious patient, which can block the airway and lead to dangerous respiratory complications. Such a situation could easily be signaled by a synthesized vomiting sound, using FOF synthesis (CSound manual, Barry Vercoe, MIT), with the quantity, nature, and location of the vomitus as piggyback variables. Similarly, synthesized coughs (short noise bursts fed to a speech synthesizer) could serve as alarms, indicating various types of respiratory complications. The realistic sound need not be a bodily sound: for example, the sound of some operating room device, such as a ventilator or blood gas analyzer could also be suitable. Accordingly, the description below is simply the current preferred embodiment of the system, which is not limited to the description below but instead by the claims which follow.

Advantageously, the sonification system may be combined with further classification or processing (e.g., a variable passing a certain threshold can still trigger an alarm or other status indicator, see below). For example, if a monitored variable exceeds a preset limit, the corresponding acoustic parameter is briefly set to its extreme value, and then returns to normal. Such a "self-labeling alarm" rapidly and efficiently informs the user that there is a problem, which monitored variable is involved, and roughly what its current values is, without being annoying or more intrusive than necessary. It may be useful to precede the alarm with a warning bell or tone to alert the user to the impending signal, or to provide a brief reference signal whereby the normal level is indicated. Such an alarm could be configured to repeat periodically until the problem is solved, or its criterion level could be readjusted if the operator deemed the current value to be acceptable. Because such a system of "self-labeling alarms" takes into account the user's needs, expectations and expertise and thus functions as a useful and efficient conduit instead of a useless annoyance, it is likely to be accepted more readily by operators, and disabled less frequently.

Advantageously, the sonification system also provides the capability of combining the normal output of the sonification system with one or more auxiliary sound sources such as recreational or background music. The system automatically maintains and adjusts the relative amplitude levels of sonification sound and auxiliary sound, taking into account alarm conditions or other important changes in variables. For instance, the level of recreational music could be set by the user to be higher than the sonification output, but the occurrence of an alarm condition would trigger a muting of the music and increase in the relative level of the sonification signal.

Advantageously, the sonification system of the present invention may further comprise means for synchronizing a visual display with the generated realistic sound representation.

Synthesis of realistic sound long predates the current invention and is currently a field of active research (e.g., physical modeling of musical instruments (Smith, "Physical Modeling using Digital Waveguides," Computer Music Journal, 16(4), 74–87 (1992), or of sonic events (Gaver 1994)). What is novel about the current method is its use of synthesized realistic sounds as a basis for abstract sonification, that is to control the variation in the acoustic parameters of a realistic sound with arbitrary data, which has no physical or analogical relationship to the change in sound. Thus, the current invention combines the ease of use and instant recognition of realistic sonification with the flexibility and extendibility of abstract sonification, thus achieving the dual goals of accessibility and power.

BRIEF DESCRIPTION OF THE DRAWINGS

These and other objects, features and advantages of the invention will be more readily apparent from the following detailed description of the preferred embodiment in which.

In the drawings, closely related figures have the same number but different alphabetic suffixes.

DETAILED DESCRIPTION OF THE PREFERRED EMBODIMENT

The current preferred embodiment of the current invention can be implemented on any of a variety of hardware platforms, e.g., a general-purpose IBM PC-compatible type personal computer using a command-line interface such as MS DOS (Microsoft Corporation, Redmond, Wash.), a Macintosh type computer (Apple Computer, Cupertino Calif.) with a graphical user interface, or on dedicated standalone hardware designed expressly for this purpose. In all cases, the same basic input, data processing, signal generation and output means are necessary. Thus the description of the preferred embodiment given here is not limited to any one of these hardware platforms, but is described in a way that one skilled in the art could implement the sonification system on any (or all) of them. For clarity of exposition, representative values are given in this description which are intended as illustrative aids and not as a limitation of any sort on the sonification system described. For example, continuous values are assumed to be normalized floating-point values in the range −1.000 to 1.000 as is standard in many signal-processing texts. However, a system based on a fixed-point DSP chip (e.g., the DSP 56001, Motorola, Phoenix, Ariz.) might use integer values instead, e.g., −4096 to 4096.

Figure 1:
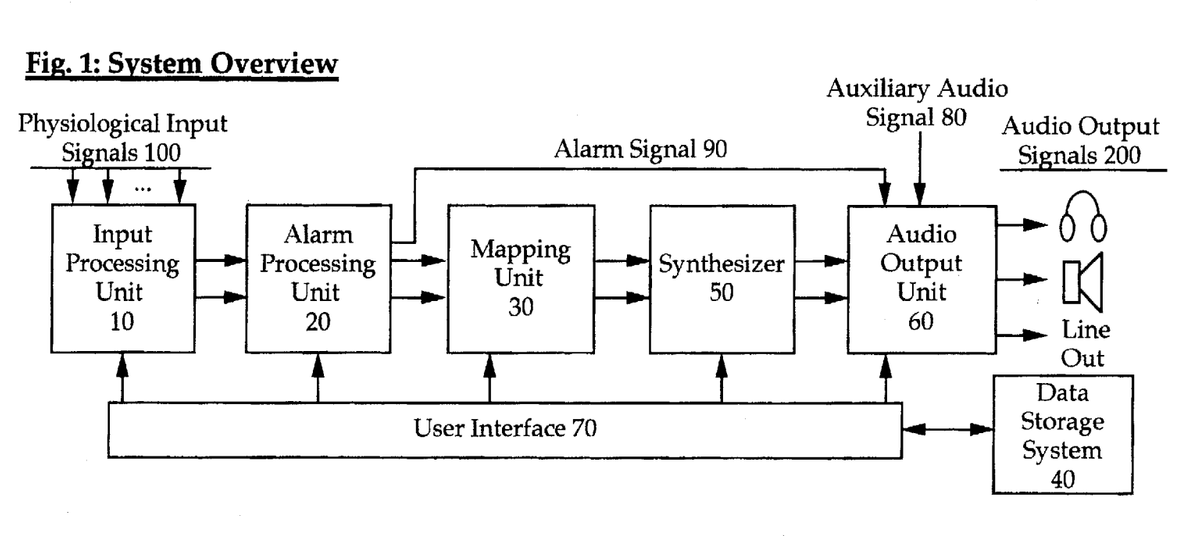
FIG. 1 shows an overview of the entire sonification system.

A typical embodiment of the sonification system described in this patent is illustrated in schematic view in schematic view in FIG. 1. Physiological input or other medically-important signals 100 enter the system via an input processing unit 10, which normalizes and conditions the data before passing it on to an alarm processing unit 20. Alarm processing unit 20 monitors the data, and signals an alarm if the data passes some user-determined thresholds. The data is then forwarded on to a mapping unit 30, which converts the data into values suitable for controlling parameters of a synthesizer 50. Synthesizer 50 converts the suitably-conditioned values from mapping unit 30 into sound, which it then transmits to an audio output unit 60. Audio output unit 60 mixes the sound synthesized by the sonification device with an optional auxiliary audio signal 80 (such as music) chosen by the user, adjusting the relative levels of these signals and adjusting their voltage into ranges suitable for use with loudspeakers, headphones or other sound-producing means. Interaction between the user and the sonification system is accomplished via a user interface 70. The user interacts via user interface 70 with a data storage system 40, which stores user-determined parameters between uses.

Physiological signals 100 can include a wide variety of measurements performed by large number of sensors and transducers (not shown). A few representative examples are given here which are not intended to limit this patent in any way. Respiration can be measured as displacement of the thorax via a pneumograph (Zemlin, Speech and Hearing Science: Anatomy and Physiology (Prentice Hall 1968) or thoracic strain gauge (Hassett, A Primer of Psychophysiology (W. H. Freeman 1978), or more directly via respirometer or volumeters (Chung & Lam 1990), which are incorporated herein by reference. Heart rate can be indicated by an electrocardiograph signal (Hasset 1978) or a peripheral or other pulse signal (U.S. Pat. No. 4,653,498, issued 1987). Oxygen saturation can be measured by an oximeter (U.S. Pat. No. 4,653,498). Exhaled carbon dioxide can be measured by a capnometer or capnograph (Chung & Lam 1990), and blood pressure can be measured by an automatic sphygmomanometer, a Swan-Ganz catheter or other arterial or venous catheters or cannulae (Chung & Lam 1990). A wide variety of further sensors are available and known to those skilled in the art and could provide input to the current invention.

Figure 2:
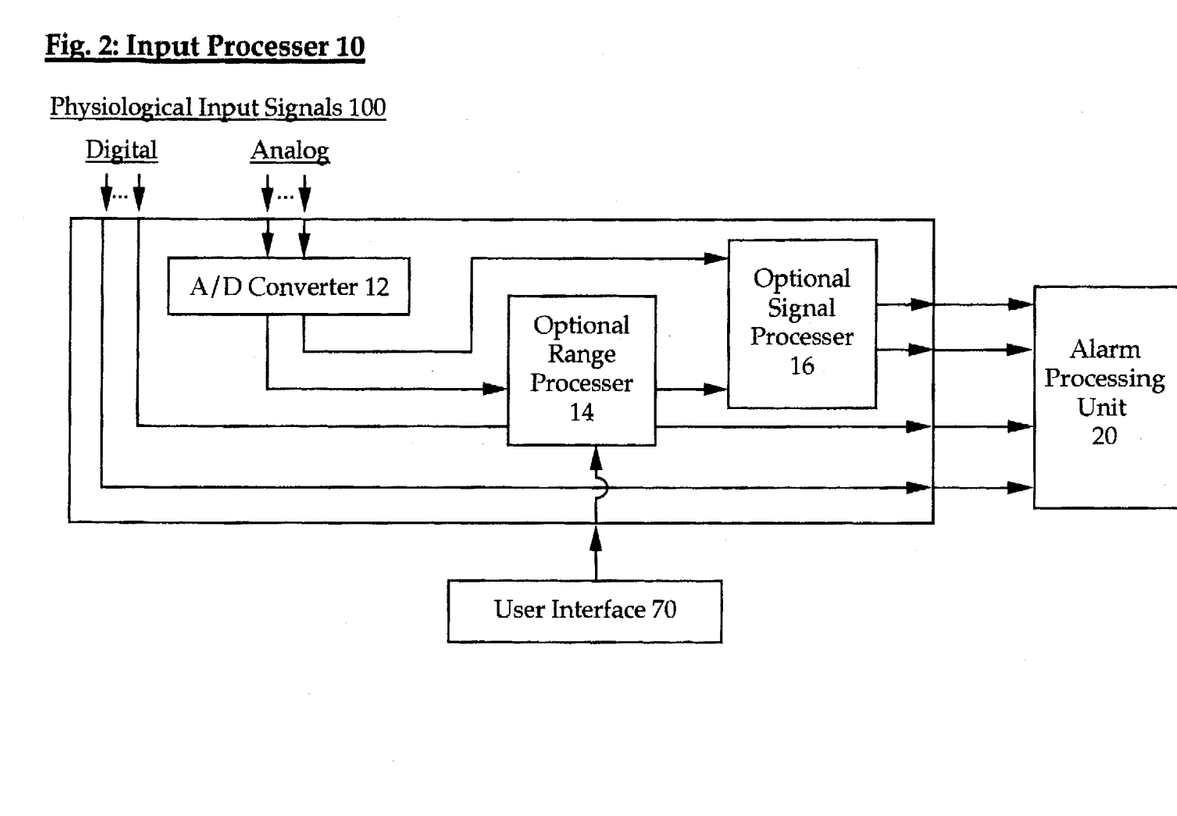
FIG. 2 provides a more detailed view of the input processing unit.

Input processing unit 10, illustrated in more detail in FIG. 2, takes in physiological signals 100 issuing from various sensors or monitoring devices in either analog or digital form. Input processing unit 10 then converts analog data to digital form using an analog-to-digital converter 12 which may include an anti-aliasing filter, as known in the art. Input processing unit 10 optionally normalizes the input data (converts to the range −1.0 to 1.0) by means of an optional range processor 14. Range processor 14 uses a user-entered offset and range for the input physiological signals, obtained via user interface 70, to accomplish this normalization. Input processing unit 10 optionally further processes this data using an optional signal processing means 16 (e.g., by thresholding or differentiating) before passing it on to alarm processing unit 20.

Figure 3:
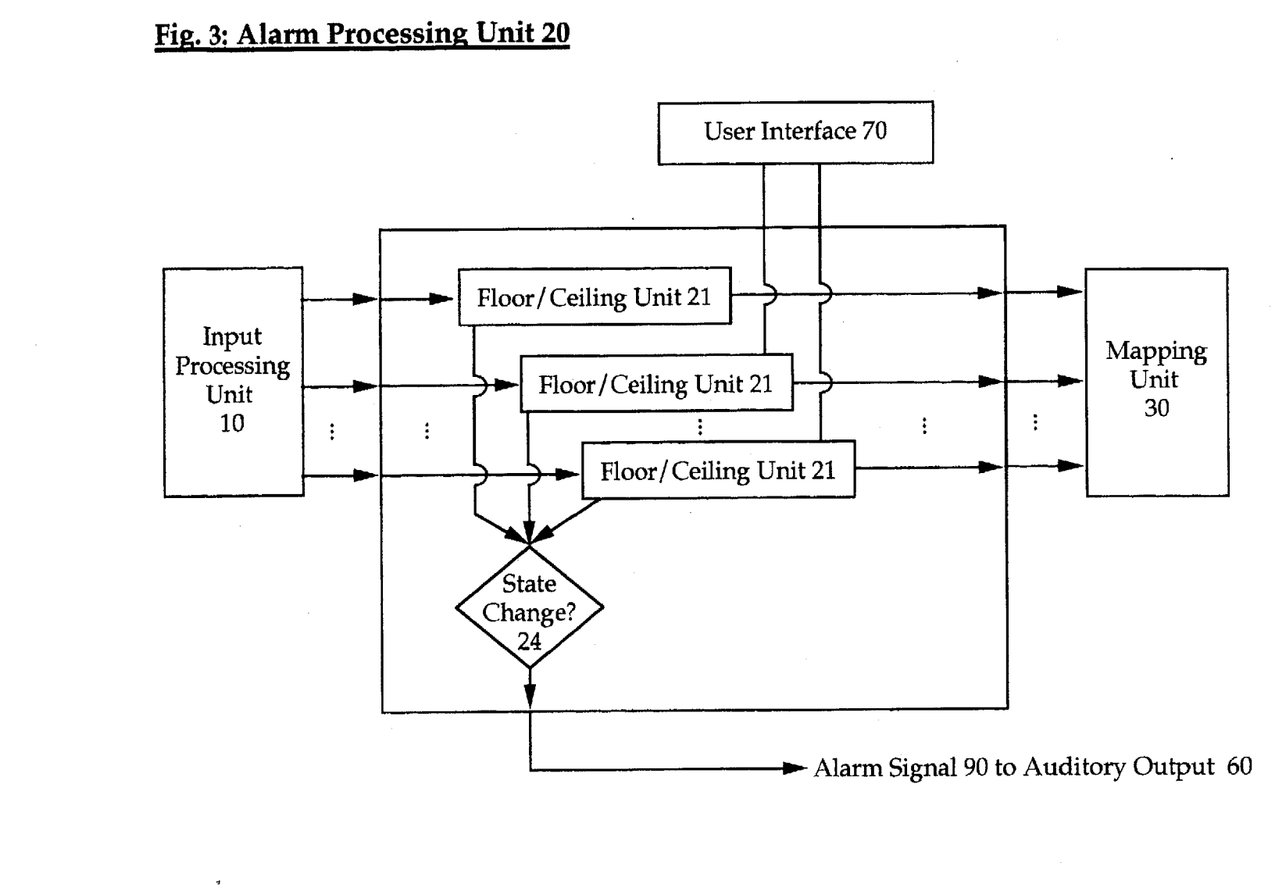
FIG. 3 gives a more detailed view of the alarm processing unit.

FIG. 3 shows alarm processing unit 20 in greater detail. The function of alarm processing unit 20 is to monitor the physiological signals and to signal the user if any of them pass over user-determined threshold values. Alarm processing unit 20 comprises a number of floor/ceiling units 21 which compare their inputs with user-determined minimum and maximum thresholds. Normally, a floor/ceiling unit 21 simply passes the value it receives at its input out through its output. However, if the input value exceeds the maximum threshold, the floor/ceiling unit 21 momentarily (e.g., for about one second) sets its output value to its maximum output value (e.g., 1.0). Similarly, if the input value drops below the minimum threshold, the floor/ceiling unit 21 momentarily (e.g., for about one second) sets its output value to its minimum output value (e.g., −1.0). The ultimate sonic result of this will be that the audio parameter corresponding to the threshold-exceeding input value will assume its extreme value momentarily, thus instantly alerting the attending personnel not only that a threshold has been crossed, but also which physiological variable is to blame and in which direction it is moving. All of the floor/ceiling units 21 also report their status (within or outside threshold) to a state change monitor 24, which registers any change in state and signals an alarm state by outputting a 1.0 value (normally state change monitor 24 outputs a 0). The values processed by alarm processing unit 20 are then passed to mapping unit 30.

Figure 4:
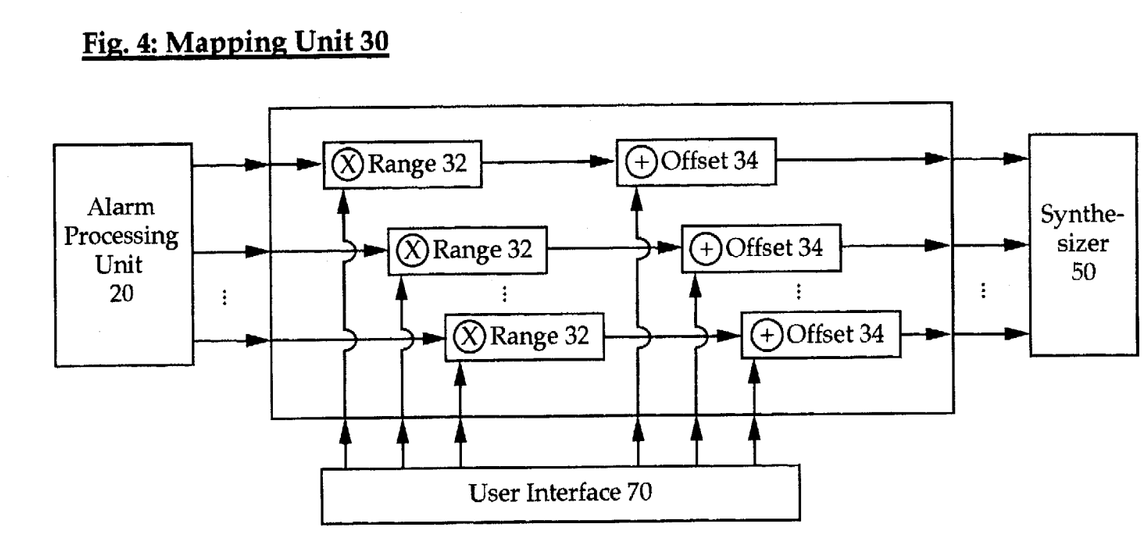
FIG. 4 provides a more detailed view of the mapping unit.

FIG. 4 shows mapping unit 30 in greater detail. The function of mapping unit 30 is to transform the physiological data into values suitable for control of synthesizer 50. Mapping unit 30 comprises a number of range multipliers 32 and offset adders 34. These simply multiply the normalized input value (which varies between −1.0 and 1.0) by an appropriate user-determined range value, and then add to the result an appropriate user-determined offset value, so as to scale the input value into a value appropriate to drive the synthesizer 50. These values are obtained from the user via user interface 70. These values, together with the pairing of physiological variables with corresponding audio parameters, constitute a data-to-sound map. This map is stored, via the user interface 70, in data storage system 40, shown in FIG. 1, which comprises a memory means (such as static RAM, a floppy disk, hard disk, or other storage means) and a retrieval means (such as a computer file system or hardwired links between data storage system 40 and the rest of the system). The values from the range/offset units, now scaled so as to be appropriate as synthesizer parameters, are then passed to the synthesizer 50.

In an alternative embodiment of the present invention, the output parameters of mapping unit 30 in FIG. 1 can be related to the input parameters by a more complex function. Such a function can be used to compensate for some human psychometric function (e.g., the Fletcher-Munson equal loudness curve), thus relating equal changes in the input variable(s) to equal perceptual changes in the output parameter(s). This complex function could be stored as a lookup table in data storage system 40. Similarly, mapping unit 30 could implement a function which combines several input variables in a prespecified way to control a single output variable.

Figure 5A:
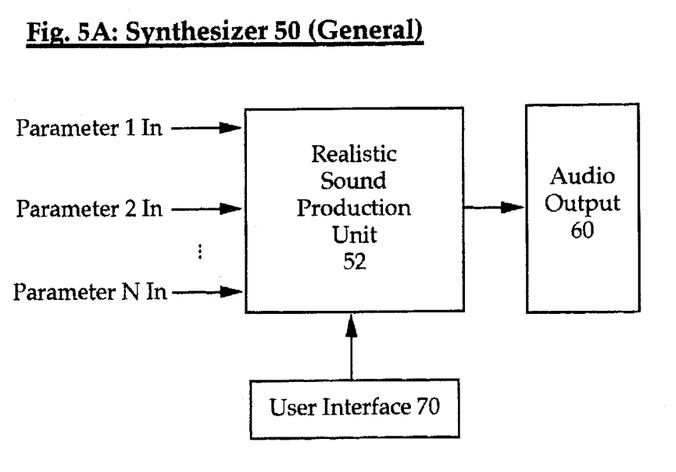
FIGS. 5A to 5E show various ways of implementing the synthesizer.
Figure 5B:
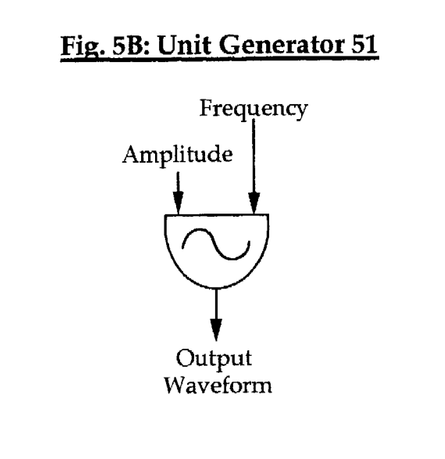

FIGS. 5A to 5E show various embodiments of synthesizer 50. FIG. 5A shows the general requirement: a plurality of inputs which control various parameters of the synthesizer algorithm which produce a realistic bodily sound. A "realistic sound" is one which can be readily recognized after an appropriate time (e.g., about a minute of play) by an intended user, not a slavish imitation of every sonic detail (see Gaver, 1994). Although the temporal qualities of such a sound (its rate and rhythm, decay function and duration, etc.) are the most important characteristics determining a sound's realism, other factors (overall pitch range, spectral composition, etc.) may also play a role. Appropriate realistic sound algorithms. could be implemented by one skilled in the art on a general purpose computer chip, e.g., the Motorola 68000 chip on a Macintosh computer, or on a digital signal processing (DSP) chip, e.g., the Motorola 56001 chip in a dedicated hardware system, or even in analog electronic form. Optionally, the user might choose among different synthesizer algorithms using user interface 70.

Figure 5C:
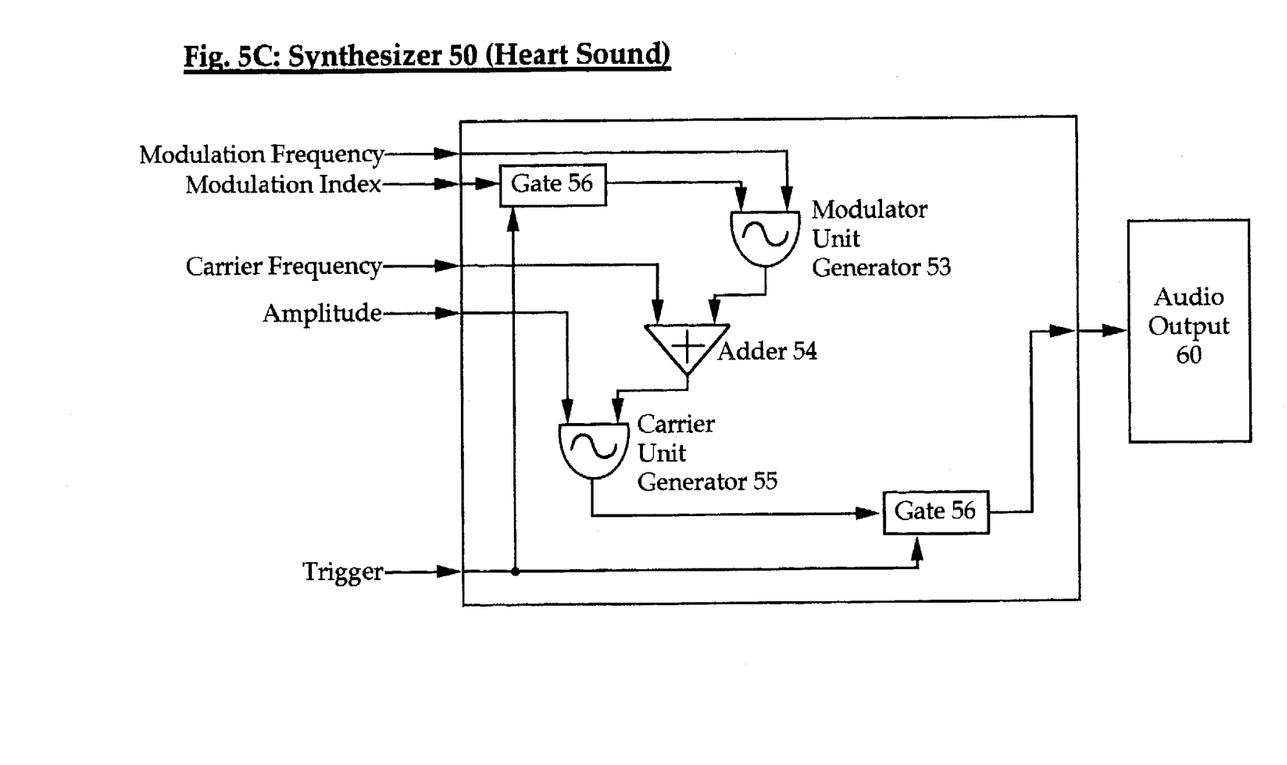

FIGS. 5B to 5E show specific examples of suitable synthesizer algorithms, using standard computer synthesis notation (see, e.g., Max V. Matthews (1969): "The Technology of Computer Music", (MIT Press, 1969), which is incorporated herein by reference. In FIG. 5C, a simple FM synthesis circuit to produce a heartbeat sound is illustrated. This circuit makes use of two "unit generators" of a type illustrated in FIG. 5B. A unit generator (e.g., unit generator 51) is a software or hardware device capable of producing an output waveform (e.g., a sine wave, square wave, or some more complex waveform) whose amplitude and frequency are continuously controllable by its left and right inlets, respectively. By combining two such unit generators in the manner shown in FIG. 5C, a frequency modulation configuration can be created comprising a modulator unit generator 53 whose output modulates the frequency of a carrier unit generator 55. The detailed operation of such a circuit is described in any introductory textbook such as Moore, Elements of Computer Music (Prentice-Hall 1990) or in Chowning "The Synthesis of Complex Audio Spectra by means of Frequency Modulation," Computer Music Journal, 46–54 (April, 1977), which are incorporated herein by reference. Chowning also gives representative values appropriate for a realistic heart sound (specifically, the "wood drum" example at page 53) as set forth in FIG. 5E. Here it will suffice to point out that changes in the amplitude of modulating unit generator 53 ("modulation index") or the frequency of modulating unit generator 53 ("modulating frequency") will lead to complex changes in the spectral content ("timbre") of the output waveform of carrier unit generator 55. Typically, the modulating frequency is maintained at a fixed percentage of the carrier frequency, so that pitch changes do not result in timbral changes. Thus, in the currently preferred embodiment, only the modulation index is used to vary timbre. To impart a natural time-varying timbre, a gate 56 can be used which imparts a time-varying envelope to the input modulation index, repeated each time a trigger pulse is received. The mean. frequency ("pitch") of the output waveform is controlled by the value given to the left side of an adder 54, which then adds to it the continuously-changing value of the modulator unit generator 53. Finally, the amplitude ("loudness") of the output waveform is controlled by the value given to the left side of carrier unit generator 55. The output of carrier unit generator 55 would be a continuous tone. To make it a series of separate sonic events separated in time like a heartbeat, a gate 56 is used. Gate 56 could be controlled by a binary trigger signal derived from a digitized EKG or pulse signal by input processor 10 via a simple thresholding operation: whenever the EKG or pulse signal exceeds a certain value, the trigger signal goes to 1, otherwise it is 0. Rather than being a simple on-off switch, gate 56 could also impart a complex amplitude envelope (e.g., a decreasing exponential curve) to its output, resulting in a more natural sound.

In accordance with the invention, several acoustic variables of the realistic heart sound generated by the synthesizer of FIG. 5C are varied in accordance with the input signals derived from sensors of various physiological variables of interest. By way of example, the repetition rate of the heart sound may be controlled by the trigger signal applied to gate 56 so that it reflects the heart rate of the patient as sensed from an EKG signal; the pitch of that sound may be controlled by a signal derived from a sensor of oxygen saturation and applied to the left input to adder 54; and the modulation index may be controlled by a signal derived from a sensor of blood pressure and applied via gate 56 to the left input to modulator unit generator 53.

Figure 5D:
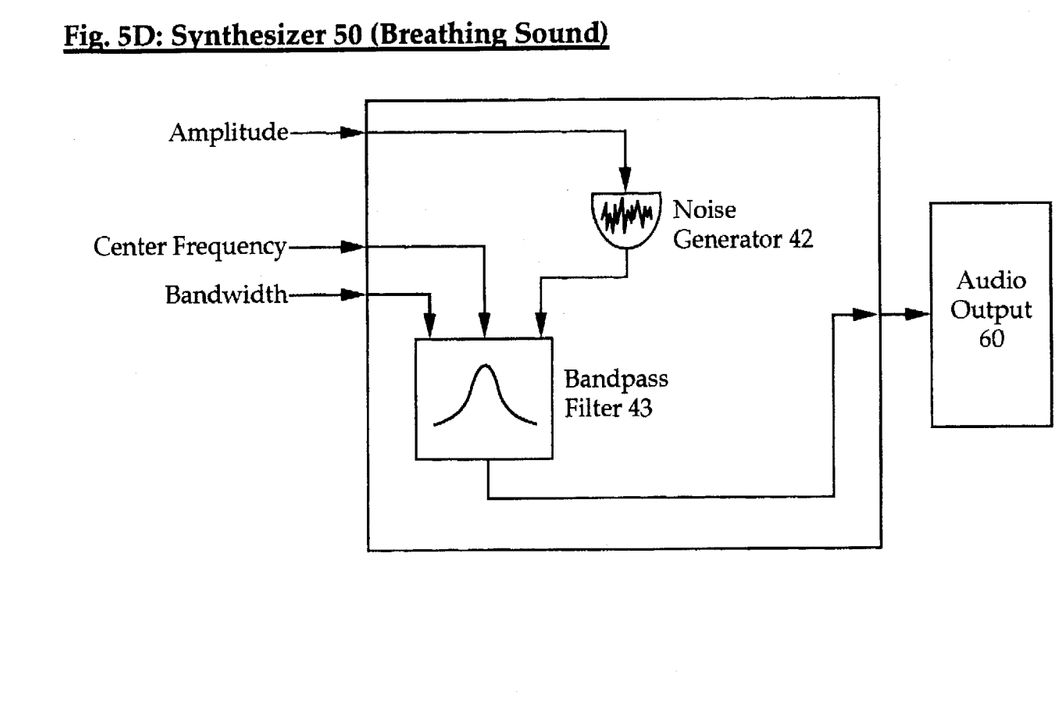
Figure 5E:
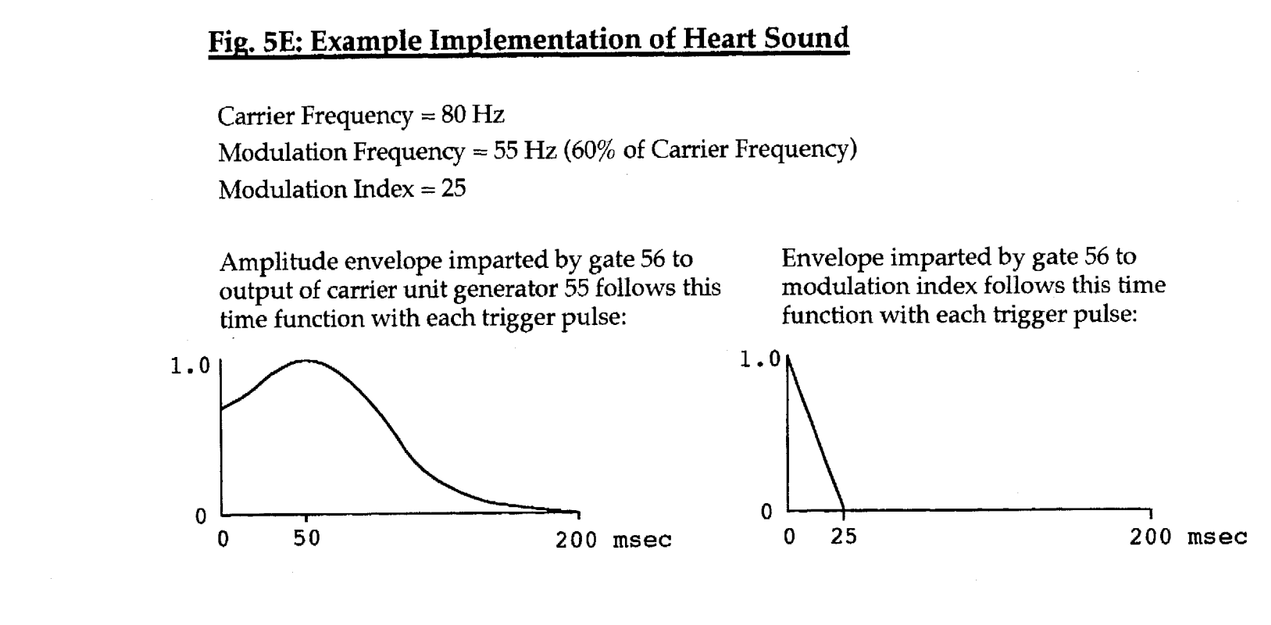

FIG. 5D shows a filtered-noise circuit capable of producing a realistic breathing sound. The output of a noise generator 42 (e.g., implemented as a random-number generator) is connected to a bandpass filter 43. A bandpass filter can be implemented as a second order filter (e.g., the two-pole IIR resonator described by Moore (1990), who also gives equations to calculate bandwidth and center frequency for such a filter). The amplitude of noise generator 42 can be controlled by the rate of change of lung volume (e.g., derived by differentiating the signal derived from a strain gauge circling the thorax, or from the readout of the ventilator volumeter, Chung & Lam (1990)), generating a signal which sounds like, and is synchronized with, the patient's breathing. The center frequency of this bandpass filter controls the perceived "pitch" of the breathing sound. The value of the center frequency is determined by a signal derived from a sensor of a second physiological variable (e.g., CO2 level). Finally, the bandwidth of bandpass filter 43 can be controlled by a signal derived from a sensor of a third physiological variable such as body temperature. Thus, in accordance with the invention, the repetition rate of the realistic breathing sound reflects the patient's respiration rate as sensed by a respirometer or the like while the perceived pitch of that sound reflects another physiological variable such as CO2 level and the bandwidth reflects body temperature.

Figure 6:
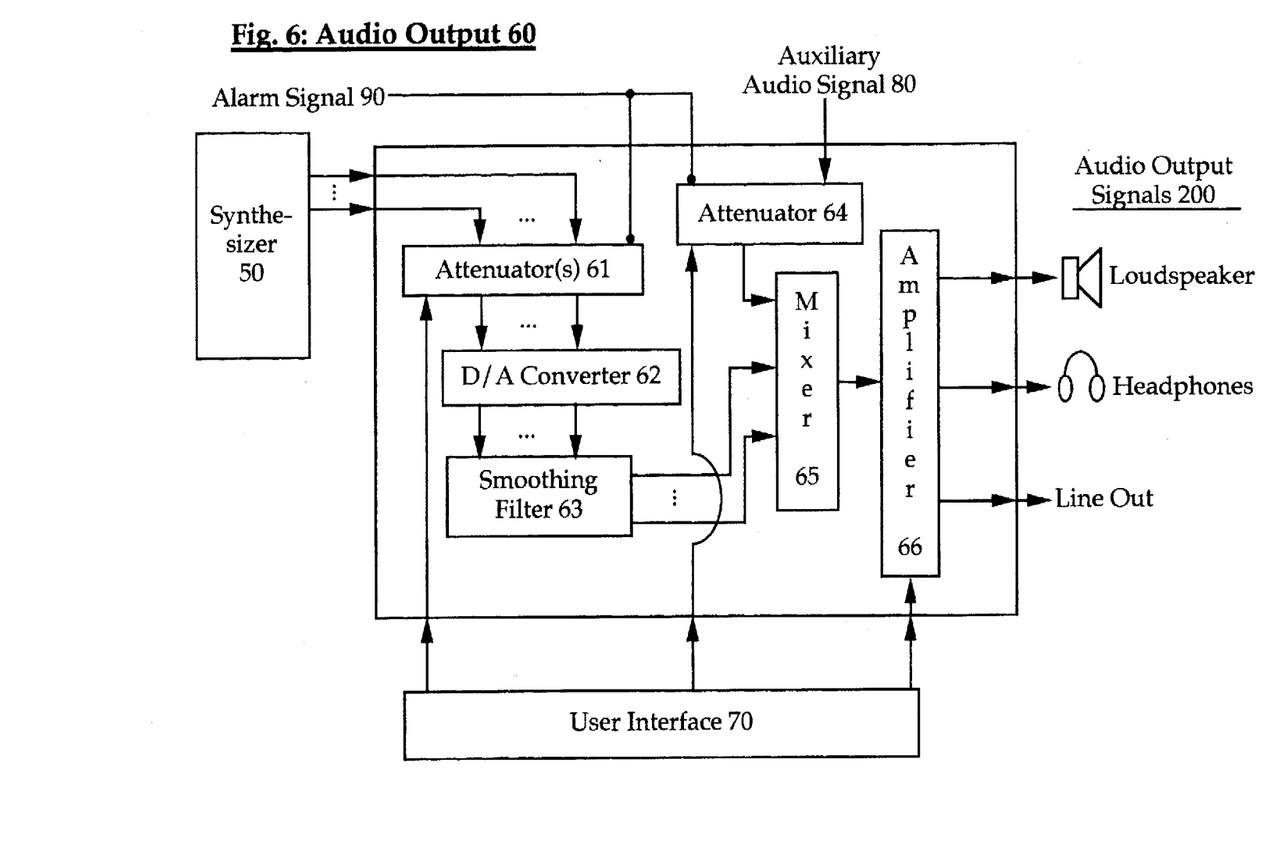
FIG. 6 provides a more detailed view of the audio output unit.

FIG. 6 provides a more detailed view of audio output unit 60. Audio output unit 60 takes the digital signal produced by synthesizer 50, adjusts its amplitude with a digital attenuator 61, and then converts it to an analog signal by passing it through a digital-to-analog converter 62 and a smoothing filter 63, preferably a lowpass or a bandpass filter. Audio output unit 60 also has the optional capability of taking in an auxiliary audio analog signal 80 and passing it through an analog attenuator 64. The relative level of the synthesizer signal versus the auxiliary audio signal 80 can be modified by the attenuators 61 and 64 in accordance with alarm signal 90, such that during an alarm the auxiliary audio signal 80 is made less loud and the synthesizer signal is made louder. The signals are added together into a monophonic or multiphonic mix by a mixer 65. The output of mixer 65 is then passed to an amplifier 66, which adjusts the voltage and amperage of the audio output signal 200 to suit any of several output devices (e.g., loudspeaker(s), headphones, or a line-out for further amplification, recording or signal processing). A loudspeaker could also be built in, in the case of some computers (i.e., Apple Macintosh) or a custom-built hardware implementation.

The manner of using the sonification system described here is similar to that of a pulse oximeter. For example, it can be installed in an operating room. It is connected to the various monitoring devices needed to measure the pertinent physiological variables (these are typically already in place in the operating room, e.g., EKG monitor, blood pressure sensor, etc.). If the user wishes to have the sound broadcast in the room for all to hear, a loudspeaker is connected to the sonification device; otherwise headphones can be used. Via user interface 70, the user sets: (a) the potential range of the input physiological variables (these may vary, e.g. for children or small animals); (b) the alarm thresholds (minimum and maximum) for each monitored parameter; (c) the ranges and offsets for each synthesizer parameter (thus the user can, for example, control the degree of timbral variation to his or her own liking) and, if desired, a more complex mapping function implemented by a lookup table; (d) the particular synthesizer modules engaged (a given implementation of this device might allow a wide variety of synthesizer circuits, allowing the user to pick a favorite, or change them periodically for variety); (e) the storage and recall of map values and the correspondence between physiological variables and acoustic parameters; (f) the overall volume, and relative levels of sonification system signal vs. auxiliary audio signal during normal operation and during an alarm state. After any of these values is entered once, it can be saved (e.g., in static RAM, or on floppy or hard disk) so that the user does not have to enter them again. As described above, this information could be entered by the user in any of a number of different ways, no one of which is necessarily superior.

Figure 7:
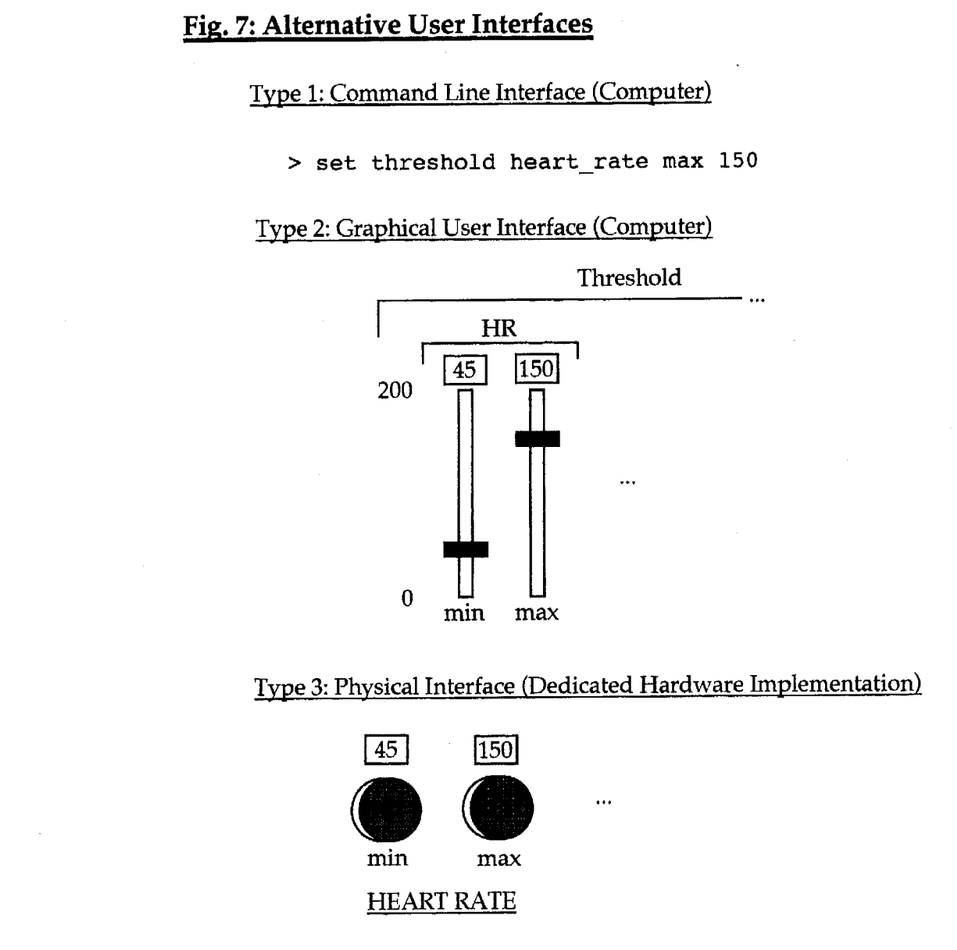
FIG. 7 shows various alternative user interfaces which could be used.

FIG. 7 shows three different types of user interface: a type 1 command line interface such as that seen in many DOS or UNIX computer programs, a graphical user interface with sliders which are manipulated by a mouse or other similar pointing device, or an actual physical interface with knobs, sliders or other input means and LCD or other similar readouts. The user interface could also be designed with visual display means synchronized with the sonification system to display the monitored physiological parameters graphically. For example, each physiological variable could control line thickness in a moving strip chart. (See Fitch and Kramer, 1994, for more detail). Other ways of synchronizing the audio system with a visual display could also be used, as known in the art. Although the description above contains many specificities, these should not be construed as limiting the scope of the invention but as merely providing illustrations of some of the presently preferred embodiments of this invention. While the examples given have related to the sonification of physiological data, it will be recognized that the invention may also be applied to the sonification of other medical data such as the output of various equipment used in operating rooms. Thus, the scope of the invention should be determined not by the examples but by the following appended claims and their legal equivalents.

I claim:

1. A sonification system for facilitating the interpretation of multi-variate physiological or medical data comprising:
    input means for receiving physiological or medical data,
    audio generating means for generating a realistic representation of bodily sound(s),
    means for varying acoustic aspects of the realistic representation in accordance with the physiological or medical input data, such that at least one variable of the input data alters the generated representation in a way literally reflective of its state and at least one variable of the input data alters the generated representation in a way only arbitrarily related to its state, wherein said means for varying further comprises automatic mixer means for combining the sound generated by the audio generating means with sounds from external sources and for controlling the amplitude level of the external sounds relative to the sounds generated by the audio generating means.

2. The sonification system of claim 1 wherein said audio generating means is capable of fine enough gradation to avoid perceptibly stepwise output.

3. The sonification system of claim 1 wherein said audio generating means comprises means for producing sound emulating the sound of breathing.

4. The sonification system of claim 1 wherein said audio generating means comprises means for producing sound emulating the sound of a heart beating.

5. The sonification system of claim 4 wherein said sound of a heart beating is generated by means of frequency modulation which has at least two variable acoustic parameters.

6. The sonification system of claim 5 wherein the audio generating means comprises means for varying amplitude, repetition rate, rhythm, modulation depth and carrier frequency of the sound of a heart beating.

7. The sonification system of claim 4 wherein said varying means maps at least one of blood pressure, oxygen saturation, and pulse strength to acoustic aspects of said sound of a heart beating.

8. The sonification system of claim 4 wherein:
   (a) heart rate is mapped to the repetition rate of the sound of a heart beating;
   (b) oxygen saturation is mapped to the pitch of the sound of a heart beating; and
   (c) blood pressure is mapped to the timbre of the sound of a heart beating.

9. The system of claim 1 further comprising means for storing and retrieving values of the input data.

10. A sonification system for facilitating the interpretation of multi-variate data comprising:
    input means for receiving data,
    audio generating means for generating sound that emulates non-artificial sound(s),
    means for varying acoustic aspects of the generated sound in accordance with input data, such that at least one variable of the input data alters the generated sound in a way literally or analogically reflective of its state, and at least one variable of the input data alters the generated sound in a way only arbitrarily related to its state,
    said means for varying including automatic mixer means for combining the sound generated by the audio generating means with sound from external sources and for controlling the amplitude level of this external sound relative to the sound generated by the audio generating means.

11. The system of claim 10 further comprising a visual display and means for synchronizing the visual display with the generated sound.

12. The system of claim 10 wherein said means for varying further comprises mapping means for controllably mapping variables of the input data to acoustic aspects of the generated sound.

* * * * *